United States Patent [19]

Duerksen

[11] Patent Number: Plant 5,715

[45] Date of Patent: Apr. 15, 1986

[54] PEACH TREE (AP-4)

[75] Inventor: Kenneth P. Duerksen, Reedley, Calif.

[73] Assignee: Alvin Peters, Reedley, Calif.

[21] Appl. No.: 667,432

[22] Filed: Nov. 1, 1984

[51] Int. Cl.[4] ..... A01H 5/00
[52] U.S. Cl. ..... Plt./43
[58] Field of Search ..... Plt./43

*Primary Examiner*—James R. Feyrer
*Attorney, Agent, or Firm*—Roger B. Webster

[57] ABSTRACT

A peach tree which is of medium size and vigor, spreading, open, vase-form and hardy; foliated with medium size, lanceolate leaves having a finely serrate margin, a petiole of medium length and thickness, and reniform glands which are small, opposite, and green; blooms with pink flowers; and is a regular and productive bearer of medium size, semi-freestone, globose fruit somewhat variable and unsymmetrical, with unequal sides; the fruit having skin of yellow ground color blushed red, and yellow flesh.

1 Drawing Figure

BACKGROUND OF THE VARIETY

1. Field of the Invention

In my supervisory capacity on a farm, including orchards, located near Reedley, Fresno County, Calif., I am responsible for the operation and maintenance of such agricultural premises, and frequent the same for the purpose of inspection and management of cultivation, irrigation, and harvesting. Against this background of activities, the present variety of peach tree was discovered by me.

2. Classification of the Variety

The present variety of peach tree is embraced by Class 43, Plants, of the United States Patent Office MANUAl OF CLASSIFICATION.

3. Prior Varieties

Among existing varieties of peach trees which are known to me and mentioned herein, are the Merrill Gemfree (U.S. Plant Pat. No. 1,409), and King's Lady (U.S. Plant Pat. No. 4,644).

ORIGIN OF THE VARIETY

The present variety of peach tree was discovered by me—growing as an open-pollinated seedling—in a King's Lady orchard on the aforesaid agricultural premises. More particularly, I observed—during a harvest, and upon the maturity of the open-pollinated seedling—that its fruit bore certain new and distinct characteristics. Subsequently, under close and continuing observation of the original tree of the present variety, I confirmed its novelty and determined to asexually reproduce such tree in anticipation of commercial growing thereof.

ASEXUAL REPRODUCTION OF THE VARIETY

The present variety of peach tree was asexually reproduced—under my direction—on the aforesaid agricultural premises by whip and tongue grafting, and—in maturity—trees so reproduced ran true to the original tree in all respects.

SUMMARY OF THE VARIETY

The present variety of peach tree is characteristically of medium size and vigor, spreading, open, vase-form and hardy; foliated with medium size, lanceolate leaves having a finely serrate margin, a petiole of medium length and thickness, and reniform glands which are small, opposite, and green; blooms in mid-February with pink flowers; and is a regular and productive bearer of medium size, semi-freestone, globose fruit somewhat variable and unsymmetrical, with unequal sides; the fruit having skin of yellow ground color blushed red, and yellow flesh.

The present variety of peach tree is further and more particularly characterized in the following respects:

The fruit of the present variety is in harvest about three days before the Merrill Gemfree; has smoother skin; and has a materially greater amount of red blush—covering substantially the entirety of the fruit; all enhancing the market-ability of the fruit.

The present variety of peach tree is still further characterized by fruit which has comparatively less split pits than the Merrill Gemfree.

Additionally, the fruit of the present variety ripens about six weeks earlier than King's Lady.

BRIEF DESCRIPTION OF THE DRAWING

The drawing is an illustration, by photographic reproduction in color, of separate fruit of the present variety; one such fruit being half cut away to expose the flesh, and with the stone remaining in place.

DESCRIPTION OF THE VARIETY

The botanical details of this new and distinct variety of peach tree—with color definitions (except those in common color terms) referenced to Maerz and Paul Dicitonary of Color (second edition)—are as follows:

Tree:
- *Size.*—Medium.
- *Vigor.*—Medium.
- *Growth.*—Spreading.
- *Density.*—Open.
- *Form.*—Vase-formed.
- *Hardiness.*—Hardy.
- *Production.*—Productive.
- *Bearing.*—Regular bearer.

Trunk:
- *Size.*—Medium.
- *Surface texture.*—Medium.

Branches:
- *Size.*—Medium.
- *Surface texture.*—Medium.

*Lenticels.*—Number — Medium. Size — Medium (Average 5 mm.×2 mm.).
*Color.*—Gray (15-C-6). Dull.

Leaves:
*Size.*—Medium. Length range — 135 mm.-140 mm. Width range — 37 mm.-39 mm.
*Form.*—Lanceolate.
*Thickness.*—Medium.
*Texture.*—Smooth.
*Color.*—Top Side — Dark green (24-L-6). Under Side — Lighter green (23-J-7).
*Margin.*—Finely serrate.
*Petiole.*—Length — Medium (Range 11 mm.-12 mm.). Width — Medium (Range 2.0 mm.-2.5 mm.).
*Glands.*—Average number — 2. Opposite. Small. Reniform. Green.

Flowers:
*Date of bloom.*—Mid-February.
*Color.*—Pink.

Fruit:
*Maturity when described.*—Eating ripe.
*Date of first picking.*—June 1st.
*Date of last picking.*—June 10th.
*Size.*—Uniform. Medium. Range diameter axially — 72 mm.-74 mm. Range transversely in suture plane — 66 mm.-68 mm.
*Form.*—Globose with unequal sides. Variable. Unsymmetrical.
*Suture.*—Distinct. Deep near base. Extends from base to apex with slight depression beyond pistil point.
*Ventral surface.*—Rounded slightly.
*Cavity.*—Rounded. Elongated in suture plane with suture showing on one side. Average depth — 10 mm. Average breadth — 16 mm. Average in suture plane — 25 mm.
*Base.*—Truncate.
*Apex.*—Rounded.
*Pistil point.*—Apical and oblique. Variable.
*Stem.*—Size — Medium (Average — 4 mm.×9 mm.).

Skin:
*Thickness.*—Medium.
*Texture.*—Medium.
*Tenacity.*—Free.
*Tendency to crack.*—Slight.
*Color.*—Ground Color — Yellow (11-G-8). Blush Color — Red (5-L-12).

Flesh:

*Color.*—Yellow (11-I-5) tinged with red (4-K-12). Surface of pit cavity — Yellow.
*Amygdalin.*—Scant.
*Juice.*—Abundant.
*Texture.*—Melting.
*Fibers.*—Few. Fine. Tender.
*Ripens.*—Evenly.
*Flavor.*—Subacid. Mild.
*Aroma.*—Distinct.
*Eating quality.*—Good.

Stone:
*Type.*—Semifree. Adheres to flesh along both dorsal and ventral edges over upper half of sides.
*Fibers.*—Short.
*Size.*—Medium. Average length — 35 mm. Average breadth — 25 mm. Average thickness — 22 mm.
*Form.*—Oval. Beaked.
*Base.*—Straight.
*Hilum.*—Narrow. Oval.
*Apex.*—Acuminate.
*Sides.*—Equal.
*Surface.*—Irregularly furrowed throughout. Ridged and pitted throughout.
*Ridges.*—Rounded.
*Pits.*—Circular and elongated.
*Ventral edge.*—Thick, with wing throughout.
*Dorsal edge.*—Narrow, with shallow, narrow groove to above center.
*Color.*—Tan (13-C-7).
*Tendency to split.*—Slight.

Use: Dessert.
Keeping quality: Good.
Shipping quality: Good.
Resistance to insects and diseases: Good.

The peach tree and its fruit herein described may vary in slight detail due to climatic and soil conditions under which the variety may be grown; the present description being of the variety as grown in the Central Valley of California.

I claim:

1. A new and distinct variety of peach tree, substantially as illustrated and described, essentially characterized by semi-freestone, yellow-flesh fruit having yellow skin blushed with red; the fruit being in harvest about three days before the Merrill Gemfree, with smoother skin, a materially greater amount of red blush, and comparatively less split pits.

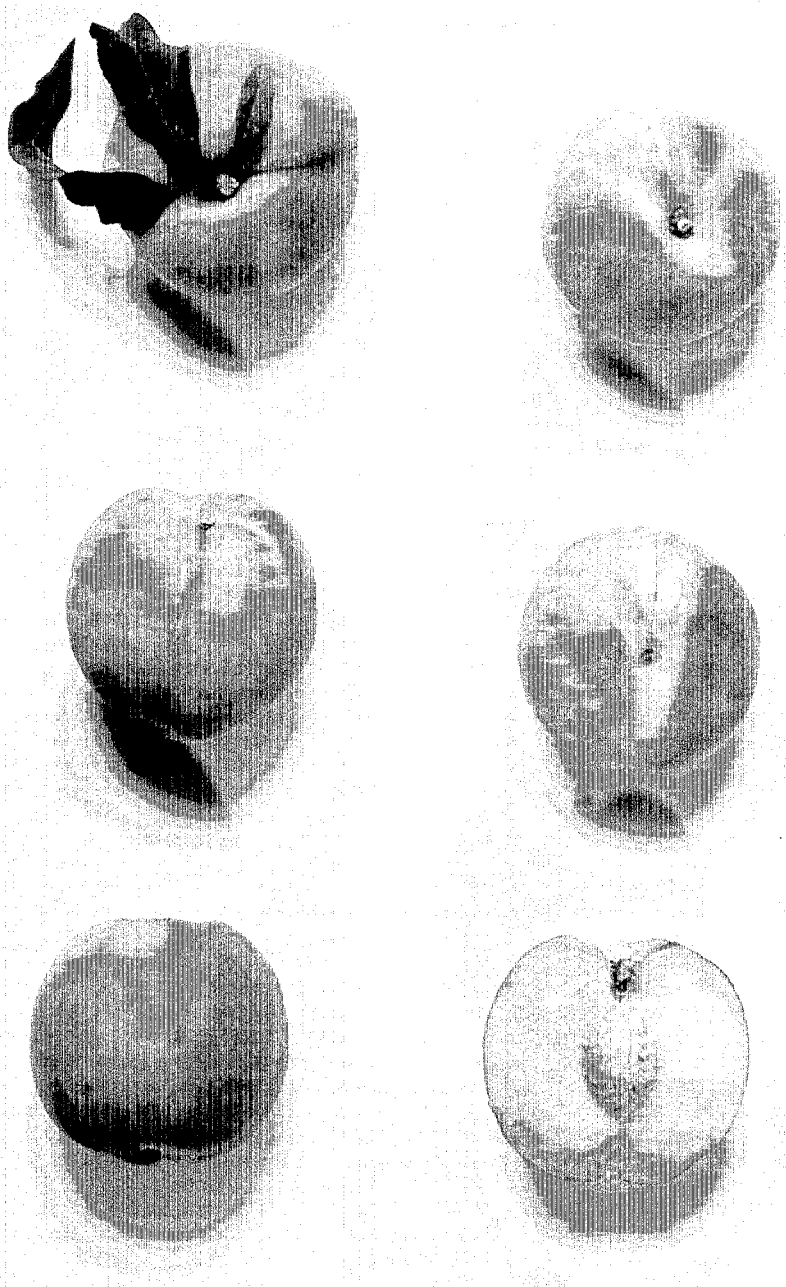

* * * * *